United States Patent [19]

Mercer et al.

[11] 3,998,219
[45] Dec. 21, 1976

[54] ORTHOPEDIC SPLINT AND METHOD FOR FORMING SAME

[75] Inventors: James D. Mercer, Lafayette; Richard G. Kvalheim, Dublin; Milton F. Custer, Livermore, all of Calif.

[73] Assignee: Hexcel Corporation, Dublin, Calif.

[22] Filed: Dec. 5, 1975

[21] Appl. No.: 637,916

[52] U.S. Cl. .............................. 128/89 R; 128/90
[51] Int. Cl.² .......................................... A61F 5/04
[58] Field of Search .................... 128/89, 90, 91 R

[56] References Cited
UNITED STATES PATENTS

| | | | |
|---|---|---|---|
| 3,656,475 | 4/1972 | Hanrahan, Jr. | 128/90 |
| 3,692,023 | 9/1972 | Phillips et al. | 128/90 |
| 3,728,206 | 4/1973 | Buese | 128/90 |

*Primary Examiner*—Louis G. Mancene
*Assistant Examiner*—Robert F. Cutting
*Attorney, Agent, or Firm*—Townsend and Townsend

[57] ABSTRACT

A honeycomb sandwich cast for supporting human or animal body portions. The cast has inner and outer cast layers which, in the finished cast, are rigid, and a central honeycomb core having honeycomb cells which are perpendicular to the skin of the underlying body portion. The honeycomb is securely attached, e.g., mechanically locked or bonded to the cast layers to form an integral, high strength, low weight honeycomb structure. An indentable, resiliently compressible fabric such as reticulated plastic foam may optionally be positioned between the faces of the honeycomb core and the cast layers. With use of such a foam, when the outer layer is applied normally by wrapping a bandage-like fabric about the body portion and the surrounding honeycomb core, a compressive force is generated which presses portions of the foam structure into the honeycomb cell openings to form a more secure interlock and prevent relative movement between the components of the cast. The foam structure can subsequently be rigidified to form a mechanical interlock between it and the honeycomb.

32 Claims, 7 Drawing Figures

ORTHOPEDIC SPLINT AND METHOD FOR FORMING SAME

BACKGROUND OF THE INVENTION

Orthopedic splints or casts are used to support body portions, normally limbs, but frequently also portions of the torso such as the rib cage, for immobilizing the underlying body portions and facilitate healing of various parts of the anatomy. Such casts have both medical and veterinary applications.

In the past, a common splint was a plaster cast. They were formed by supplying bandages covered with plaster of paris, immersing the bandages in water immediately prior to their application, and thereafter wrapping the bandages about the body portions in question, say a leg. After the plaster of paris hardens, a rigid cast is formed. Casts often carry weight and are subject to a certain amount of abuse during daily use. They must therefore be relatively thick, in the order of one inch or more. This represents great bulk and weight which has to be carried around by the patient and greatly restricts his mobility. Moreover, plaster of paris is brittle, breaks upon impact, and deteriorates when subjected to moisture. Even though its characteristics are substantially less than one might desire, plaster casts are widely used because of the simplicity with which they can be applied and because they are relatively inexpensive.

Some of the shortcomings experienced with plaster casts were overcome by orthopedic splints made from a plastic webbing or fabric which is wrapped about the leg. The fabric is solidified by first applying a solvent so that surface areas of the fabric are liquefied. After the solvent evaporates, the dissolved fabric material solidifies again and forms a rigid matrix since portions of the fabric loops in contact with each other fuse together. This cast or splint and certain improvements and variations thereof are illustrated and described in U.S. Pat. Nos. 2,308,483; 2,373,802; 2,489,252; and 2,632,442. (hereinafter sometimes referred to as "fabric patents").

As is more fully set forth in U.S. Pat. No. 2,489,252, suitable plastic materials include cellulose plastic such as cellulose esters, cellulose ethers; polystyrene plastics; and vinyl ester plastics such as polyvinyl acetate, polyvinyl chloride, polyvinyl chloride acetate and copolymers of vinyl acetate, and vinyl chloride. Solvents for such materials include ethyl acetate, acetone, methyl acetate, methyl formate, and others.

Another approach utilizing plastic materials as a replacement for plaster casts is the impregnation into a backing web such as a gauze or fabric of a fusible plastic material. The plastic impregnated web is wrapped around the broken limb after which it is heated, molded and cooled to form a relatively rigid cast. As more fully described in the U.S. Pat. No. 3,692,023, suitable fusible plastic materials may include blends of cyclic ester polymers such as poly-epsilon-caprolactone and poly-(vinyl alkyl ethers) such as poly-(vinyl ethyl ether). Use of heat fusible materials eliminates the need for solvent activation.

Splints made in this manner are substantial improvements over plaster casts insofar as their overall weight, strength, and moisture resistance is concerned. However, they require relatively expensive raw materials so that such splints are not always as economical as one might desire.

The prior art has also made attempts to improve orthopedic splints by using more lightweight materials such as corrugated cardboard, air inflatable splints or splint sections, and reusable splints. As far as the present invention is concerned, splints employing corrugated materials are the most pertinent. U.S. Pat. Nos. 3,750,660 and 3,656,475 are exemplary. In essence, they show sandwich constructions in which an inner and an outer sheet are separated by a corrugated material having flutes or cells which run essentially parallel to the skin over which the splint is applied. These splints, although of light weight and relatively inexpensive, are primarily temporary splints for field applications. Their strength is very limited, they are normally incapable of resisting moisture, and, on the whole, they are not for permanent use, that is, use for several days up to several months.

SUMMARY OF THE INVENTION

The present invention provides an improved orthopedic splint or cast and a method for applying it. Generally speaking, the cast of the present invention is a honeycomb sandwich cast having a first, inner cast layer placed over the skin of the body portion to be supported, a central honeycomb core, and an outer cast layer. The cast layers are securely interlocked with and/or bonded to the honeycomb core via a suitable adhesive to prevent relative movements therebetween. To further this purpose, the cells of the honeycomb extend perpendicular to the underlying skin and to the cast layers. Optionally a separate locking member such as an indentable or resiliently compressible material may be interposed between faces of the honeycomb and the respective cast layers. The compressible material may be a reticulated plastic foam or other suitable compressible material. When the outer cast layer is applied, a compressive force is generated between the resiliently compressible material and the honeycomb core, thereby forcing portions of the foam into the cells and forming a combined frictional-mechanical interlock. To provide a positive mechanical interlock, the foam can be rigidified after the application of the outer cast layer. Alternatively, the compressible material can be bonded to the core and the cast layers or the cast layers can be directly bonded to the honeycomb core to define the desired honeycomb sandwich structure.

This sandwich construction of the cast permits the use of relatively thin inner and outer cast layers, which may be constructed of a variety of materials such as conventionally applied plaster of paris or, preferably, of a water impervious, moisture resistant material such as the bonded plastic fabric disclosed in the above-referenced fabric patents. A strength increase can be obtained both by increasing the thickness of the honeycomb core, which adds very little to the weight of the cast, and by increasing the thickness of the respective cast layers. Moreover, a strength increase is observed by rigidifying the interlocking compressible layers. This can be done by coating the compressible layer initially with plaster of paris and then hardening the plaster of paris as by spraying it with water just prior to or after the outer cast layer is applied.

By orienting the honeycomb cells so that they are perpendicular to the cast layers and the underlying skin, the honeycomb direction exhibiting strength is utilized for rendering the cast rigid, supporting weight as when the cast is used as a walking cast on the lower leg of a patient, or resisting impact against the outer cast layer. Moreover, the undulated ribbon defining the honeycomb has sharp edges at the honeycomb faces which project with a relatively large unit pressure into the interlocking foam which such a layer is utilized. They are therefore relatively deeply imbedded therein and form a secure interlock without any further action. And by rigidifying the deformed foam, or other compressible material, a positive mechanical interlock is obtained.

Adequate bonds can also be obtained directly between the honeycomb core and the rigid inner and outer layers without resort to a separate intermediate layer. In the case of solvent activated plastic webbing or fabric such as those taught in the previously referenced U.S. Pat. No. 2,489,252, a sheet of solvent activated adhesive between the core and fabric may be used to enhance the bond. In the case of heat softened plastic webbing such as that taught in previously referenced U.S. Pat. No. 3,692,023, a hot melt adhesive may be used to obtain good bonds. Finally, where conventional plaster layers are used, additional plaster may be applied to insure good bonds to the honeycomb.

In short, adequate bonds can be obtained by directly contacting the honeycomb core to the heat, solvent or water activated rigid layers or a separate bonding layer such as a thin adhesive layer or a resilient thicker layer may be employed.

The cast or splint of the present invention is a substantial improvement as compared to the prior art and it applies the well known advantages of a sandwich structure to orthopedic splints. Its weight is normally no more than about one-third to one-fourth of the weight of a plaster cast having a comparable strength. Further, the great reduction in weight renders the splint economically competitive with the much heavier prior art casts even though it employs base materials which, on a weight basis, are more expensive than plaster of paris, for example. Furthermore, the splint can be constructed of moisture resistant and water-impervious materials so that the heretofore common deterioration of the casts during daily use, particularly when exposed to water, is eliminated. The splint materials can be impact resistant materials such as the earlier mentioned plastic fabrics, so that the splint does not deteriorate even during extended use. Thus, a splint constructed in accordance with the present invention can be worn for many months without requiring replacement. Such replacement was frequently necessary with prior art casts.

DESCRIPTION OF THE PREFERRED EMBODIMENTS

Figure 1:
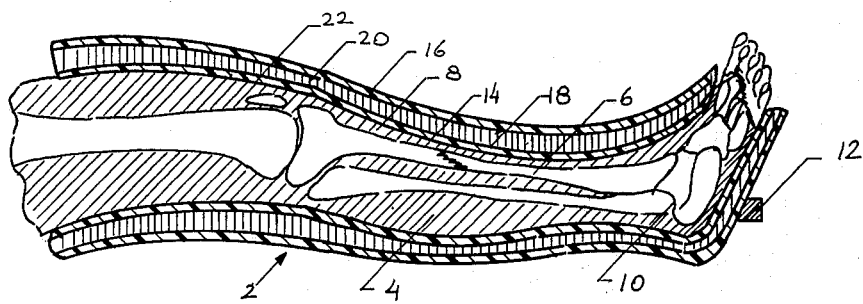
FIG. 1 is a longitudinal, sectional view of the splint of the present invention applied to immobilize a human leg.
Figure 2:
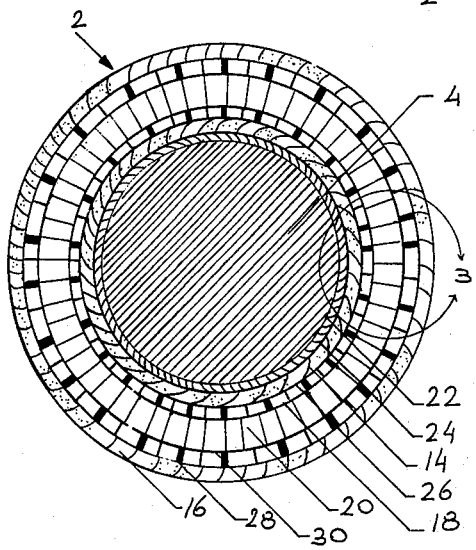
FIG. 2 is an enlarged, cross-sectional view taken on line 2—2 of FIG. 1 and illustrates the relative positioning and placement of the components making up the honeycomb sandwich splint of the present invention.
Figure 3:
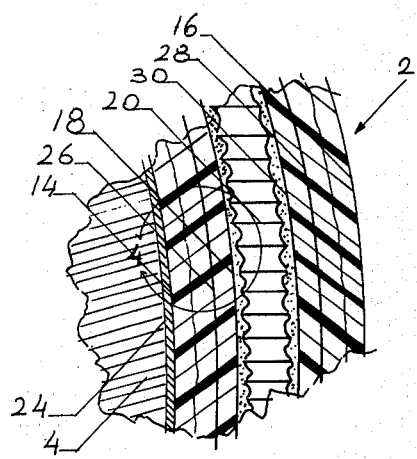
FIG. 3 is an enlarged, fragmentary, cross-sectional view illustrating in greater detail the construction of the splint of the present invention.

Referring first to FIG. 1, a cast or splint 2 constructed in accordance with the present invention is shown applied to a human leg 4, having a broken tibia 6 and requiring the immobilization of knee 8 and ankle 10. The cast is intended as a walking cast and is provided with a suitable walking heel or shoe 12 which supports the cast and the leg on the ground when the patient takes a step. The cast is a sandwich cast defined by inner and outer cast layers 14, 16 and an intermediate honeycomb core 18 having core cells 20 which are oriented perpendicular to skin 22 of the patient's leg 4 and, therewith, also to the cast layers.

The honeycomb core may be of a conventional construction and have repeating hexagonal cells defined by undulated ribbons which are bonded to each other at their common nodal points. Such honeycomb is relatively stiff, and for application of the cast to relatively sharply curved body portions, such as the human leg, it is preferred to employ three-dimensionally deformable honeycomb. The construction of such honeycomb is fully set forth in U.S. Pat. No. 3,227,600 and it is commercially available from the Hexcel Corporation of Dublin, California. The honeycomb may be constructed of a variety of materials but for purposes of light weight and moisture resistance it is preferred to use honeycomb constructed of aluminum foil. If desired, however, impregnated paper honeycomb, plastic honeycomb, and the like may be substituted.

Referring now to FIGS. 1 through 4, the construction and application of cast 2 is described in detail. After the body portion to be supported by the cast, e.g., leg 4, has been set in the position in which it is to be immobilized, a protective sheath such as a stockinette 24 is applied to separate the skin (and any hair growing thereof) from the actual cast, as is conventional in the art. Thereafter, padding material such as crepe paper, webbing, foam, or the like, may be applied to cushion and protect the leg and skin from the cast and to prevent possible rubbing between them.

The first cast layer 14 is now applied, preferably by using a bandage comprising a fabric or webbing of a plastic material which can thereafter be solvent or heat softened as, for example, described in the above-referenced issued fabric patents. Normally, the bandage is supplied in rolls of up to six inches in width and the roll, if solvent activated, is briefly immersed in suitable solvent. Thereafter the bandage is quickly wrapped about the leg and stockinette. In normal practice it is most desirable to form the inner cast layer with two passes of the roll over the leg. The layer then will have a thickness of between 1/32 and 1/16 inch.

Upon completion of the formation of the inner cast layer, the core is bonded to the cost layer. In one form of the invention, an indentable, resiliently compressible material of the required width and length is placed over the inner layer. The material may comprise reticulated plastic foam such as reticulated urethane foam. Applying the core or foam to the inner cast layer before the latter fully dries, or cools, that is before the solvent thereon fully evaporates, or the fusible plastic fully solidifies assures the formation of a bond between the two. In the case of foam, surface bonding together with frictional forces generated between the foam and the inner cast layer prevents relative movement.

Since the foam layer should be permeable, reticulated or open core foam is preferred, although open cell and closed cell foam can be employed. Furthermore, since the foam layer is subsequently compressed by the intermediate honeycomb core 18 and should partially protrude into the open core cells, it should have a thickness of at least about 1/16 inch. A range of about 1/32 to 1/8 inch is fully acceptable. Thinner foams normally provide insufficient indentability, and padding, whereas thicker foam layers add undesirably to the bulk of the finish formed cast and permit excessive limb movement.

After the inner cast layer has been wrapped with inner foam layer 26, honeycomb core 18 is applied. When the cast exhibtis relatively sharp curvatures, a three-dimensionally deformable honeycomb core is employed. It is cut to a width so that when wrapped around the leg it substantially fully encircles it and to a length so that it extends from above the knee to at least the ankle. Excess length may be provided to extend the same honeycomb core over the heel to the patient's foot. Alternatively, a second, smaller core section may be applied over the foot.

The core is manually held in position or may be temporarily tightened as with string or tape. Thereafter an outer cast layer is applied over the core, or when an outer foam layer 28 is wrapped about outer face 30 of the core the outer cast layer 16 is formed over the outer foam layer. Again, the outer cast layer if it is solvent activated is applied by first briefly soaking a plastic fabric roll in a suitable solvent and thereafter wrapping it around the outer foam layer to form the outer cast layer 60. Normally, two or three passes are preferred to give the outer cast layer sufficient strength to resist normally expected impact from sharp corners, edges, and the like during the every day use of the cast. After the outer cast layer has been fully formed by making the desired number of passes with the roll, drying of the outer cast layer and set-up in the case of solvent activated rolls may be speeded up by directing a hot air stream against the cast, while in the case of heat softenable rolls, fusion and set-up is accomplished by heating the material to above its softening temperature and allowing it to cool.

While the outer cast layer is applied, or separately thereafter, walking heel 12 is conventionally applied by positioning it against the under side of the cast and securing it thereto as by wrapping it with a plastic fabric after it has been briefly placed in a suitable solvent.

This completes the formation of the cast and after all solvent has evaporated, the plaster has set or the softenable material has fully solidified, the cast has reached its full strength and rigidity and is ready for use, e.g., for walking thereon. The finish formed cast is a honeycomb sandwich which exhibits the beneficial strength-to-weight ratio attained with such structures. The rigidly spaced apart inner and outer layers form a structure capable of resisting large tension, compression and bending forces. If the inner and outer cast layers were not so spaced apart, the strength of the cast would be greatly reduced and with the indicated layer thicknesses such a cast would be incapable of providing the desired support and leg immobilization.

Figure 4:
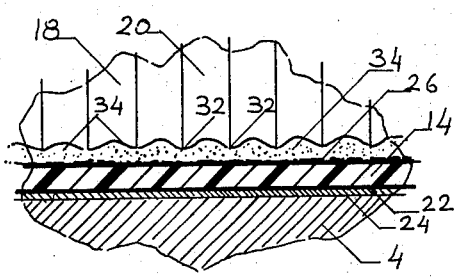
FIG. 4 is a further enlarged, cross-sectional view illustrating the interlock between the honeycomb core, the rigid inner cast layers, and the indentable, resiliently compressible foam interposed between the two.

As is illustrated in FIG. 4, the purpose of the foam layers 26, 28 is to form a mechanical interlock between the core and the cast layers not always obtainable using only surface bonding techniques. When the outer cast layer is formed, the roll of plastic fabric is tensioned and wrapped around the leg while under such tension. This generates an inwardly directed radial compressive force against the outer foam layer 26, core 18, and inner foam layer 26 which is supported by the already rigidified inner cast layer 14. Sharp edges 32 of the honeycomb core 18 exert a large unit pressure against the foam layers and indent therein so that the resiliently compressible foam between the honeycomb edges springs back and protrudes into core cells 20. Since the foam layers are immovably retained to the cast layers, foam protrusions 34 in the honeycomb cells have the effect of forming an interlock between the foam and the core so that relative movement between them along their interfaces is prevented. For many applications no more is needed to form an effective, immovable connection between all layers of the cast.

In instances where the applied loads are relatively large, as on walking casts for example, it may become desirable to form a more positive interlock between the core and the foam. Such an interlock can be established by rigidifying the foam after it has been indented, that is, after the outer cast layer 16 has been applied. In one form of the invention, foam layers 26, 28 are therefore covered with plaster of paris. It is most desired that the plaster of paris adheres to all ligaments. This can be accomplished by dusting the foam immediately prior to use with plaster of paris or by adhering the plaster of paris with a suitable bonding agent which prevents a premature set-up of the plaster.

Plaster coated foam is applied to the cast in the same manner as described above. However, after its application, the foam is wetted as by spraying water over the cast after the inner and outer cast layers have set up and hardened. The plaster adhering to the foam will then harden the foam in its deformed position (as shown in FIG. 4) so that foam protrusions 34 become essentially non-compressible. A secure mechanical interlock between the plaster and the foam is thereby established.

Alternative methods of rigidifying the resilience of the compressible foam can of course be employed. Thus, the foam may be treated with suitable chemical agents to cause its hardening after it has been compressed. Such procedures are well within the purview of those skilled in the art and, therefore, not further described herein.

Such an interlock can also be established by bonding the foam to the honeycomb core and the adjacent cast layer as by applying a bonding agent or subjecting the foam to a solvent which renders it temporarily tacky. Upon the evaporation of the solvent, which is preferably the same as the solvent used in the plastic bandages used for forming the cast layers, the foam adheres to both the core and the cast layers. Alternatively, the cast layers can be directly bonded to the honeycomb core, thereby eliminating the intermediate foam layers.

For orthopedic applications, a honeycomb thickness of 3/16 to 1/4 inch for the above-described cast is normally sufficient for honeycomb having a cell size of between 1/8 inch to 3/8 inch and made of aluminum foil. The finished cast then has an overall thickness of about 1/2 inch to 3/4 inch. If desired, the honeycomb may be supplied in thinner form so that it can be applied in multiple layers as by spirally winding them about the leg to attain the desired thickness. In such instances, the honeycomb core may be a full length sheet or it may be furnished in narrower bands which are then wrapped about the leg in a fashion similar to the wrapping of a bandage.

Figure 5:
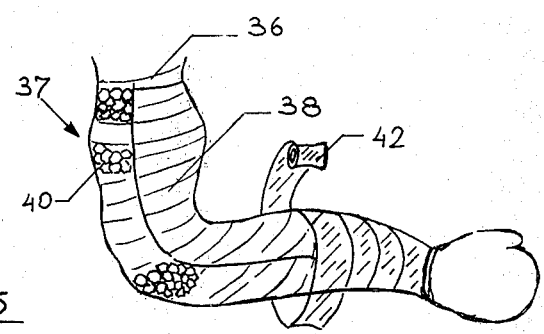
FIG. 5 is a schematic, fragmentary view illustrating the manner in which a splint constructed in accordance with the present invention may be applied to a human arm.
Figure 6:
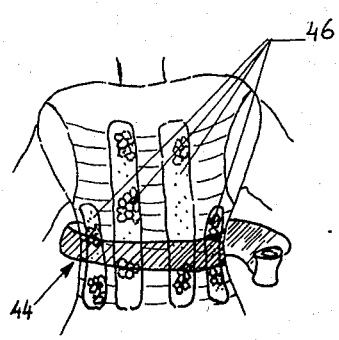
FIG. 6 is a schematic, fragmentary view illustrating the manner in which the splint of the present invention can be applied to a human torso.
Figure 7:
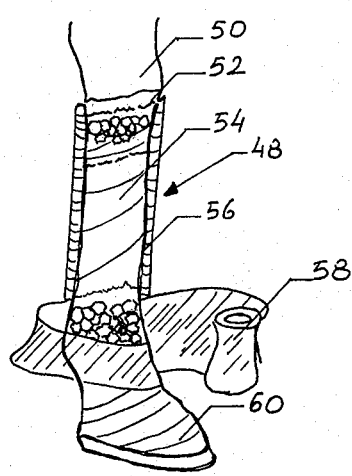
FIG. 7 is a fragmentary, schematic view illustrating the manner in which the splint of the present invention can be applied to an animal foot.

Referring now briefly to FIGS. 5 through 7, various applications of the cast of the present invention are illustrated. In FIG. 5, a honeycomb sandwich cast 37 is formed on a human arm 36 by first forming an inner cast layer 38 as above described, thereafter positioning the honeycomb core 40 over the layer and then wrapping a roll 42 of the above-referenced plastic fabric, for example, as above described to complete the cast. Foam layers (not separately shown in FIG. 5) are positioned between the inner and outer cast layers and the intermediate honeycomb core.

In FIG. 6, a honeycomb sandwich cast 44 is formed to support and protect a human torso. The cast is applied by forming inner and outer cast layers and positioning therebetween a honeycomb core, in the illustrated instance a plurality of sectional cores 46 which are shaped and positioned to follow the counter and provide the desired cast rigidity. Intermediate foam layers as above described are included.

Casts 37 and 44 illustrated in FIGS. 5 and 6 both depart from the cast shown in FIGS. 1–4 in that the intermediate honeycomb core does not fully surround the body member to which the cast is applied. Instead, the honeycomb core is strategically positioned, as over the elbow in FIG. 5 and at certain locations distributed about the circumference of the torso in FIG. 6, to obtain the desired rigidity and cast strength. In both instances those portions of the arm and torso, respectively, over which it is difficult and/or bulky to apply a honeycomb core are covered with the combined inner and outer cast layer only. This is particularly advantageous in applications where relatively little load and force is applied to the cast.

Referring now briefly to FIG. 7, a honeycomb sandwich cast 48 constructed in accordance with the invention is applied to a body portion of an animal, say a leg 50 of a horse. The cast is applied as described above in connection with the description of FIGS. 1–4. In particular, prior to the application of an inner cast layer a protective wrap, such as a paper layer and s stockinette 52 are applied to the leg. Thereafter a plastic bandage is immersed in a solvent and rolled about the leg to form an inner cast layer 54.

Next a honeycomb core 56 is placed over the inner cast layer (after the application of an intermediate foam layer, not separately shown in FIG. 7) an outer foam layer is placed over the exterior surface of the honeycomb core and finally a plastic bandage 58 is wrapped about the outer foam layer to form an outer cast layer 60. After the outer cast layer has dried (as above described), the cast is completed and forms a high strength cast ready to support heavy loads.

In view of the relatively greater forces applied to a cast on the leg of a heavy animal such as a horse, the cast will normally have larger dimensions than a corresponding human cast. Thus, both the inner and outer cast layers may be substantially thicker than above described and honeycomb 56 may have a thickness of as much as ½ inch or more, giving the finished cast an overall thickness of up to one inch or more.

What is claimed is:

1. An orthopedic cast for placement over a body member comprising a first, inner layer of a substantially rigid material placed over the member, a second, outer layer of substantially rigid material disposed over the first layer, a honeycomb core disposed between the layers and having cells extending generally perpendicular to the layers, the inner and outer layers being attached to the honeycomb core to prevent relative movements therebetween along their respective interfaces.

2. A cast according to claim 1 wherein the honeycomb core comprises a three dimensionally deformable honeycomb.

3. A cast according to claim 1 wherein the honeycomb comprises hexagonal honeycomb.

4. A cast according to claim 1 wherein the honeycomb comprises a single honeycomb core disposed between the layers.

5. A cast according to claim 1 wherein the honeycomb core comprises a plurality of stacked honeycomb cores disposed between the layers.

6. A cast according to claim 5 wherein the inner and outer layers define an annular space therebetween, and wherein the honeycomb is spirally wrapped about the inner layer.

7. A cast according to claim 1 wherein an interlocking means is employed between the honeycomb and at least one of the substantially rigid layers.

8. A cast according to claim 7 wherein the interlocking means comprises a resiliently compressible material disposed between at least one of the substantially rigid layers and an adjacent face of the honeycomb so that portions of the compressible material protrude into the cells to thereby form an interlock between the compressible material and the cells.

9. A cast according to claim 8 including means for securing the compressible material to the respective layers.

10. A cast according to claim 8 wherein the compressible material comprises foam material, and including means for rigidifying the foam material in its resiliently compressed state in which the portions protrude into the cells to thereby form a mechanical interlock.

11. A cast according to claim 10 wherein the rigidifying means comprises a relatively thin layer of plaster adhering to ligaments of the foam.

12. A cast according to claim 11 wherein the foam is bonded to at least one of the substantially rigid layers and the adjacent face of the honeycomb.

13. A cast according to claim 12 wherein the interlocking means comprises a bonding agent bonding the layers to adjacent faces of the honeycomb core.

14. A lightweight, high-strength rigid orthopedic cast comprising an inner cast layer placed over a body portion, an intermediate honeycomb core having cells perpendicular to the inner layer, an outer cast layer overlying the honeycomb core, and a resiliently compressible material placed intermediate each layer and an adjacent side of the honeycomb core, the outer layer including means generating compressive forces between the core and the compressible materials, parts of the compressible material being displaced into honeycomb core cell openings to form a mechanical interlock between the honeycomb and the material and to thereby prevent relative movements between the two along their interfaces.

15. A cast according to claim 14 including means rigidifying portions of the compressible materials displaced into the honeycomb cell openings.

16. A cast according to claim 14 wherein the inner and outer cast layers include plaster of paris as a rigidifying agent.

17. A cast according to claim 14 wherein the inner and outer cast layers include a multiplicity of individual, rigidly interconnected plastic members.

18. A lightweight, high-strength, rigid orthopedic cast for placement over the skin of a body portion comprising: a tubular honeycomb sandwich adapted to be placed about the body portion and defined by a central honeycomb core having honeycomb cells oriented substantially perpendicular to the skin; an inner face sheet placed between the core and the member and constructed of a relatively thin, substantially water impervious and rigid material; an outer face sheet placed over an outer side of the core and constructed of a relatively thin, substantially water impervious and rigid material; and means substantially immovably attaching the face sheets to the core.

19. An orthopedic cast comprising an inner, relatively thin and substantially rigid cast layer placed over a body portion to be supported; an intermediate honeycomb core having cells disposed perpendicular to the skin of the body portion, a first indentable material placed over an outer face of the core; a second indentable material disposed in a space between an inner face of the core and inner cast layer; a substantially rigid outer cast layer formed by applying the outer cast layer over the first indentable material and compressing the first indentable material against the outer core face to thereby generate a compressive force between the outer cast layer and the inner cast layer and indent portions of the indentable material into corresponding openings of the honeycomb cells to thereby engage all layers and form a rigid cast.

20. A cast according to claim 19, including means for rigidifying the indentable material after the application of said compressive force to thereby form a mechanical interlock between the honeycomb core and the indentable material.

21. A method for forming a lightweight, high-strength honeycomb sandwich orthopedic cast over a body portion to be supported by the cast and in substantial conformity with the contour of said body portion comprising: applying a first cast layer over the body portion to be supported; bonding a honeycomb core to the first cast layer sich that the cells of this core are oriented substantially perpendicular to the skin of the body portion; bonding a second cast layer to the outer face of the honeycomb core; and rigidifying at least the first and second cast layers to finish form the cast.

22. A method according to claim 21 wherein the steps of forming the first and second cast layers comprises the steps of wrapping about the body portion and about the honeycomb material, respectively, a dissolvable fabric, dissolving toughing portions of fabric with a solvent, and evaporating the solvent after the respective wrapping steps.

23. A method according to claim 21 wherein the steps of forming the first and second cast layers comprises the steps of wrapping about the body portion and the honeycomb material, respectively, a fusible fabric, heating the fabric to cause it to fuse and allowing the fabric to cool to rigidify the first and second layers.

24. A method according to claim 21 wherein the steps of forming at least one of the first and second cast layers comprises the step of forming the layers of plaster of paris.

25. A method according to claim 21 wherein the honeycomb core is bonded to the first and second cast layers via first and second indentable materials, said first indentable material being applied over the first cast layer and the second indentable material being applied over an outer face of the honeycomb core; compressing the indentable materials against the core by wrapping over the second indentable material a second cast layer to thereby generate compressive forces with such second cast layer.

26. A method according to claim 25 including the step of rigidifying the indentable material after the application of the compressive forces and a consequent deformation of the material.

27. A method according to claim 26 wherein the indentable material comprises a reticulated foam structure, and wherein the step of rigidifying comprises the step of applying a hardenable substance to the reticulated foam, and hardening the substance after the application of the compressive forces.

28. A method according to claim 27 wherein the hardenable substance comprises plaster of paris and including the step of attaching to the reticulated foam structure a thin layer of plaster of paris, and wherein the step of hardening comprises the step of contacting the plaster of paris with water.

29. A method for forming a lightweight, high-strength orthopedic cast comprising the steps of:
    placing a first, deformable layer of a material over a body portion to be supported by the cast;
    placing a honeycomb core over a deformable material so that honeycomb core cells are substantially perpendicular to the skin underlying the cast;
    placing a second layer of a deformable material over an exterior face of the honeycomb core;
    engaging and interlocking the deformable materials with the honeycomb core to prevent relative movements between the materials and the core at their respective interfaces;
    and rigidifying the engaged deformable materials to thereby form a rigid, strong and lightweight cast.

30. A method according to claim 29 wherein the step of rigidifying comprises the step of applying to the deformable material plaster of paris and hardening the plaster of paris after it has been interlocked with the honeycomb core.

31. A method according to claim 29 wherein the step of rigidifying comprises the steps of applying a pliant material to sides of the deformable material facing away from the honeycomb core, and rigidifying the pliant material to form a rigid sandwich having the deformable material disposed between the rigidified pliant material and the core.

32. A method according to claim 21 including the step of rigidifying the deformable material.

* * * * *